(12) United States Patent
Abe et al.

(10) Patent No.: US 10,513,644 B2
(45) Date of Patent: *Dec. 24, 2019

(54) TWO-PACK CURABLE URETHANE ADHESIVE COMPOSITION

(71) Applicant: The Yokohama Rubber Co., LTD., Minato-ku, Tokyo (JP)

(72) Inventors: Megumi Abe, Hiratsuka (JP); Yuichi Matsuki, Hiratsuka (JP); Takanori Kido, Hiratsuka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/580,664

(22) PCT Filed: Jun. 12, 2015

(86) PCT No.: PCT/JP2015/067060
§ 371 (c)(1),
(2) Date: Dec. 7, 2017

(87) PCT Pub. No.: WO2016/199298
PCT Pub. Date: Dec. 15, 2016

(65) Prior Publication Data
US 2018/0163103 A1     Jun. 14, 2018

(51) Int. Cl.
| | |
|---|---|
| *C09J 175/04* | (2006.01) |
| *C09J 11/06* | (2006.01) |
| *C07C 11/21* | (2006.01) |
| *C09J 11/08* | (2006.01) |
| *C08G 18/63* | (2006.01) |
| *C08G 18/64* | (2006.01) |
| *C08G 18/69* | (2006.01) |
| *C08G 18/20* | (2006.01) |
| *C08G 18/24* | (2006.01) |
| *C08G 18/28* | (2006.01) |

(52) U.S. Cl.
CPC .............. *C09J 175/04* (2013.01); *C07C 11/21* (2013.01); *C08G 18/2027* (2013.01); *C08G 18/248* (2013.01); *C08G 18/282* (2013.01); *C08G 18/632* (2013.01); *C08G 18/6492* (2013.01); *C08G 18/69* (2013.01); *C09J 11/06* (2013.01); *C09J 11/08* (2013.01)

(58) Field of Classification Search
CPC .............................. C07C 11/21; C09J 175/04
See application file for complete search history.

(56) References Cited

U.S. PATENT DOCUMENTS

| | | | | |
|---|---|---|---|---|
| 4,533,598 A | * | 8/1985 | Downey | ............ C08G 18/0842 156/48 |
| 2017/0260434 A1 | | 9/2017 | Yokohama Rubber | |

FOREIGN PATENT DOCUMENTS

| | | |
|---|---|---|
| EP | 3 208 321 | 8/2017 |
| JP | 2003-171641 | 6/2003 |
| JP | 2007-031483 | 2/2007 |
| JP | 2013-104018 | 5/2013 |
| JP | 2014-025000 | 2/2014 |
| JP | 2015-131940 | 7/2015 |
| WO | 2016/080508 | 5/2016 |

OTHER PUBLICATIONS

International Search Report for International Application No. PCT/JP2015/067060 dated Sep. 1, 2015, 4 pages, Japan.
European Search Report for European Application No. 15894983.4 dated Jul. 8, 2019, 6 pages, Germany.

\* cited by examiner

*Primary Examiner* — Mark S Kaucher

(57) ABSTRACT

A two-part curable urethane adhesive composition of the present technology contains a base agent containing a urethane prepolymer, and a curing agent containing a compound having two or more active hydrogen groups in each molecule. The curing agent contains at least one type of terpene compound selected from the group consisting of monoterpenes, hydrogenated monoterpenes, modified monoterpenes formed by modifying the monoterpenes or the hydrogenated monoterpenes with hydroxy groups, and oligomers having from 2 to 6 repeating units derived from the monoterpenes or the modified monoterpenes.

20 Claims, No Drawings

TWO-PACK CURABLE URETHANE ADHESIVE COMPOSITION

TECHNICAL FIELD

The present technology relates to a two-part curable urethane adhesive composition.

BACKGROUND ART

In recent years, resin materials (e.g. olefin-based resins, and matrix resins of fiber reinforced plastic (FRP)) have been used for automobile bodies in place of steel plates from the perspective of reducing weight.

Adhesion of such a resin material with a different type of raw material (e.g. glass) has been typically performed by using a primer after the resin material has been subjected to flame processing (e.g. see Japanese Unexamined Patent Application Publication Nos. 2007-031483 and 2013-104018).

However, problems of negatively affecting environment exist because a primer contains a large amount of solvent.

SUMMARY

The present technology provides a two-part curable urethane adhesive composition that exhibits excellent adhesion to a resin material without the use of a primer.

The inventors of the present technology have found that a two-part curable urethane adhesive composition containing a particular terpene compound in a curing agent component exhibits excellent adhesion to a resin material, and thus completed the present technology.

Specifically, the inventors of the present technology found that the problems described above can be solved by the following features.

[1] A two-part curable urethane adhesive composition containing: a base agent containing a urethane prepolymer, and a curing agent containing a compound having two or more active hydrogen groups in each molecule; the curing agent containing at least one type of terpene compound selected from the group consisting of monoterpenes, hydrogenated monoterpenes, modified monoterpenes formed by modifying the monoterpenes or the hydrogenated monoterpenes with hydroxy groups, and oligomers having from 2 to 6 repeating units derived from the monoterpenes or the modified monoterpenes.

[2] The two-part curable urethane adhesive composition according [1], where the monoterpene is a compound represented by Formula (1), a compound represented by Formula (2), or a compound represented by Formula (3);

the hydrogenated monoterpene is a compound represented by Formula (4);

the modified monoterpene is a compound represented by Formula (5), a compound represented by Formula (6), or a compound represented by Formula (7); and the oligomer is a compound represented by Formula (8), a compound represented by Formula (9), or a compound represented by Formula (10).

[3] The two-part curable urethane adhesive composition according to [1] or [2], where a content of the terpene compound is from 1 to 30 mass % relative to the total mass of the curing agent.

[4] The two-part curable urethane adhesive composition according to any one of [1] to [3] above, where the curing agent contains a polybutadiene diol as the compound having two or more active hydrogen groups in each molecule.

[5] The two-part curable urethane adhesive composition according to any one of [1] to [4] above, where the curing agent contains a rosin diol as the compound having two or more active hydrogen groups in each molecule.

[6] The two-part curable urethane adhesive composition according to any one of [1] to [5] above, where the base agent further contains an isocyanate silane compound.

[7] The two-part curable urethane adhesive composition according to [1] above, where the curing agent contains a polyol compound as the compound having two or more active hydrogen groups in each molecule; and the two-part curable urethane adhesive composition is used for adhesion to a resin material using no primer.

[8] The two-part curable urethane adhesive composition according to [1] above, where the terpene compound is at least one type selected from the group consisting of monoterpenes, hydrogenated monoterpenes, and modified monoterpenes formed by modifying the monoterpenes or the hydrogenated monoterpenes with hydroxy groups.

Advantageous Effects of Technology

According to the present technology, a two-part curable urethane adhesive composition that exhibits excellent adhesion to a resin material without the use of a primer can be provided.

DETAILED DESCRIPTION

The two-part curable urethane adhesive composition of the present technology (hereinafter, also abbreviated as "the adhesive composition of the present technology") is a two-part curable urethane adhesive composition containing: a base agent containing a urethane prepolymer, and a curing agent containing a compound having two or more active hydrogen groups in each molecule; the curing agent containing at least one type of terpene compound selected from the group consisting of monoterpenes, hydrogenated monoterpenes, modified monoterpenes formed by modifying the monoterpenes or the hydrogenated monoterpenes with hydroxy groups, and oligomers having from 2 to 6 repeating units derived from the monoterpenes or the modified monoterpenes.

In the present technology, as described above, excellent adhesion to a resin material (especially an olefin resin) is achieved by allowing a particular terpene compound to be contained in the curing agent component.

Although the details are not clear, this is because the miscibility of the terpene compound and a non-polar moiety in the curing agent (e.g. polyol compound described below) becomes excellent, thereby making the adhesion between a surface of a resin material and the non-polar moiety excellent when the resin material is adhered.

Base Agent

The base agent of the adhesive composition of the present technology contains a urethane prepolymer.

Furthermore, the base agent preferably contains isocyanate silane described below.

Urethane Prepolymer

A urethane prepolymer contained in the base agent of the adhesive composition of the present technology is a polymer containing a plurality of isocyanate groups at a molecular terminal in each molecule.

A conventionally known urethane prepolymer can be used as such a urethane prepolymer. For example, a reaction product, obtained by reacting a polyisocyanate compound with a compound having two or more active hydrogen groups in each molecule (hereinafter, abbreviated as "active hydrogen compound") so that the amount of the isocyanate group is in excess relative to the amount of the active hydrogen groups can be used.

Polyisocyanate Compound

The polyisocyanate compound used during the production of the urethane prepolymer is not particularly limited as long as the polyisocyanate compound has two or more isocyanate groups in each molecule.

Specific examples of the isocyanate used in the polyisocyanate compound include aromatic polyisocyanates such as TDI (e.g. 2,4-tolylene diisocyanate (2,4-TDI) and 2,6-tolylene diisocyanate (2,6-TDI)), MDI (e.g. 4,4'-diphenylmethane diisocyanate (4,4'-MDI) and 2,4'-diphenylmethane diisocyanate (2,4'-MDI)), 1,4-phenylene diisocyanate, polymethylene polyphenylene polyisocyanate, xylylene diisocyanate (XDI), tetramethylxylylene diisocyanate (TMXDI), tolidine diisocyanate (TODI), 1,5-naphthalene diisocyanate (NDI), and triphenylmethane triisocyanate; aliphatic polyisocyanates such as hexamethylene diisocyanate (HDI), trimethylhexamethylene diisocyanate (TMHDI), lysine diisocyanate, and norbornane diisocyanate (NBDI); alicyclic polyisocyanates such as transcyclohexane-1,4-diisocyanate, isophorone diisocyanate (IPDI), bis(isocyanate methyl)cyclohexane ($H_6$XDI), and di cyclohexylmethane diisocyanate ($H_{12}$MDI); carbodiimide-modified polyisocyanates thereof; isocyanurate-modified polyisocyanates thereof; and the like.

Such a polyisocyanate compound may be used alone, or a combination of two or more types of these polyisocyanate compounds may be used.

Among these, MDI is preferable from the perspective of excellent curability.

Active Hydrogen Compound

The active hydrogen compound having two or more active hydrogen groups in each molecule that is used during the production of the urethane prepolymer is not particularly limited.

Preferred examples of the active hydrogen compound include polyol compounds having two or more hydroxy (OH) groups in each molecule, polyamine compounds having two or more amino groups and/or imino groups in each molecule, and the like. Among these, a polyol compound is preferable.

The polyol compound is not particularly limited with respect to its molecular weight, skeleton, and the like as long as the polyol compound is a compound having two or more OH groups. Specific examples thereof include low-molecular-weight polyhydric alcohols, polyether polyols, polyester polyols, other types of polyols, polyol mixtures thereof, and the like.

Specific examples of the low-molecular-weight polyhydric alcohols include low-molecular-weight polyols such as ethylene glycol (EG), diethylene glycol, propylene glycol (PG), dipropylene glycol, 1,3-butanediol, 1,4-butanediol, pentanediol, neopentyl glycol, hexanediol, cyclohexanedimethanol, glycerin, 1,1,1-trimethylolpropane (TMP), 1,2,5-hexanetriol, and pentaerythritol; sugars such as sorbitol; and the like.

As the polyether polyols and polyester polyols, compounds derived from the low-molecular-weight polyhydric alcohols are typically used, but in the present technology, compounds derived from aromatic diols, amines, and alkanolamines described below may also be favorably used.

Here, specific examples of the aromatic diols include resorcin (m-dihydroxybenzene), xylylene glycol, 1,4-benzene dimethanol, styrene glycol, 4,4'-dihydroxyethyl phenol; compounds having bisphenol skeletons of a bisphenol A structure (4,4'-dihydroxyphenylpropane), a bisphenol F structure (4,4'-dihydroxyphenylmethane), a brominated bisphenol A structure, a hydrogenated bisphenol A structure, a bisphenol S structure, or a bisphenol AF structure described below; and the like.

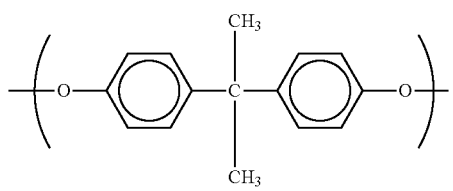

BISPHENOL A STRUCTURE

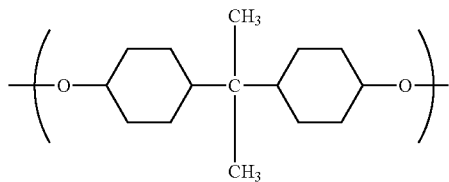

HYDROGENATED BISPHENOL A STRUCTURE

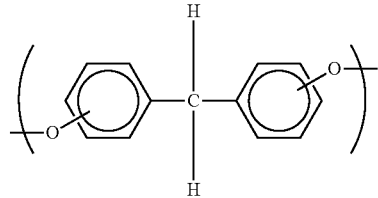

BISPHENOL F STRUCTURE

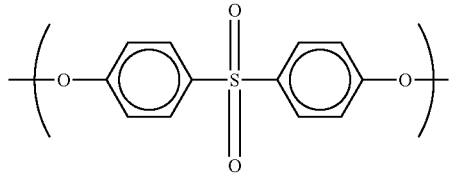

BISPHENOL S STRUCTURE

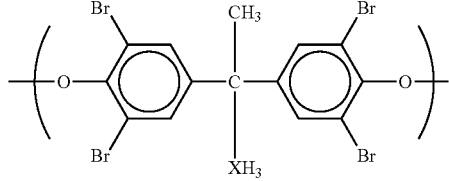

BROMINATED BISPHENOL A STRUCTURE

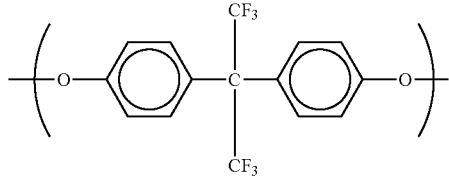

BISPHENOL AF STRUCTURE

Additionally, specific examples of the amines include ethylenediamine, hexamethylenediamine, and the like. Specific examples of the alkanolamines include ethanolamine, propanolamine, and the like.

Examples of the polyether polyols include polyols obtained by adding at least one type selected from styrene oxide, alkylene oxides such as ethylene oxide, propylene oxide, butylene oxide (tetramethylene oxide), and tetrahydrofuran, or the like, to at least one type selected from the compounds that are exemplified as the low-molecular-weight polyhydric alcohols, the aromatic diols, the amines, and the alkanolamines described above; and the like.

Specific examples of the polyether polyol include polyethylene glycol, polypropylene glycol (PPG), polypropylene triol, ethylene oxide/propylene oxide copolymers, polytetramethylene ether glycol (PTMEG), polytetraethylene glycol, sorbitol polyol, and the like.

Likewise, examples of the polyester polyol include the condensation products (condensed polyester polyols) of any of the low-molecular-weight polyhydric alcohols, the aromatic diols, the amines, or the alkanolamines with a polybasic carboxylic acid; lactone polyols; polycarbonate polyols; and the like.

Specific examples of the polybasic carboxylic acid which may be used here to form the condensed polyester polyol include glutaric acid, adipic acid, azelaic acid, fumaric acid, maleic acid, pimelic acid, suberic acid, sebacic acid, phthalic acid, terephthalic acid, isophthalic acid, dimer acid, pyromellitic acid, other low-molecular-weight carboxylic acid, oligomeric acid, castor oil, hydroxycarboxylic acid such as a reaction product of castor oil and ethylene glycol (or propylene glycol), and the like.

In addition, specific examples of the lactone polyols include compounds that are obtained by ring-opening polymerization of a lactone such as ε-caprolactone, α-methyl-ε-caprolactone, or ε-methyl-ε-caprolactone with a suitable polymerization initiator, and that have hydroxy groups at both ends.

Specific examples of other polyol include acrylic polyol; polybutadiene diol; polymeric polyol having carbon-carbon bonds on the main chain skeleton, such as hydrogenated polybutadiene polyol; and the like.

In the present technology, the various polyol compounds exemplified above may be used alone or may be used in a combination of two or more types.

Among these, the polyol compound is preferably polypropylene glycol from the perspective of achieving excellent balance of hardness and elongation at break of the adhesive composition of the present technology containing the resulting urethane prepolymer as the base agent as well as achieving excellent cost.

Specific examples of the polyamine compound include aliphatic polyamines such as ethylenediamine, propylenediamine, butylenediamine, diethylenetriamine, tri ethylenetriamine, triethylenetetramine, tetraethylenepentamine, pentaethylenehexamine, hexamethylenediamine, trimethylhexamethylenediamine, 1,2-propanediamine, iminobispropylamine, methyliminobispropylamine, and 1,5-diamino-2-methylpentane (MPMD, manufactured by Dupont K.K.); aromatic polyamines such as meta-phenylenediamine, ortho-phenylenediamine, para-phenylenediamine, m-xylylenediamine (MXDA), diaminodiphenyl methane, diaminodiphenyl sulfone, and diamino diethyldiphenylmethane; N-aminoethylpiperazine; monoamine having an ether bond in its main chain, such as 3-butoxyisopropylamine; diamines having a polyether backbone, that are exemplified by JEFFAMINE EDR148 manufactured by Sun Techno Chemicals Co., Ltd.; alicyclic polyamines such as isophoronediamine, 1,3-bisaminomethylcyclohexane (1,3BAC, manufactured by Mitsubishi Gas Chemical Company, Inc.), 1-cyclohexylamino-3-aminopropane, and 3-aminomethyl-3,3,5-trimethyl-cyclohexylamine; diamines having a norbornane backbone, such as norbornanediamine (NBDA, manufactured by Mitsui Chemicals, Inc.); polyamide amines having an amino group at a molecular terminal of polyamide; 2,5-dimethyl-2,5-hexamethylene diamine, menthenediamine, 1,4-bis(2-amino-2-methylpropyl)piperazine, JEFFAMINE D230 and JEFFAMINE D400, manufactured by Sun Techno Chemicals Co., Ltd., having polypropylene glycol (PPG) as a backbone; and the like. These polyamine compounds may be used alone or may be used in a combination of two or more types.

Among these, diamine having a polyether backbone (JEFFAMINE) and hexamethylene diamine are preferable.

Isocyanate Silane

The base agent of the adhesive composition of the present technology preferably contains isocyanate silane together with the urethane prepolymer from the perspective of achieving superior adhesion of the adhesive composition of the present technology.

The isocyanate silane is a compound having an isocyanate group and a hydrolyzable silicon-containing group and, for example, can be obtained by reacting an isocyanate group-containing compound and a compound having a functional group that can be reacted with the isocyanate group and having a hydrolyzable silicon-containing group.

Preferred examples of the isocyanate silane compound includes, specifically, compounds obtained by reacting diisocyanate, such as MDI and TDI, with a silane coupling agent, such as an aminoalkoxysilane and a mercaptoalkoxysilane.

Furthermore, an isocyanate silane compound obtained by reacting the isocyanate group-containing compound described in JP 2002-053798 A with a silane coupling agent having an imino group in which a phenyl group or a derivative thereof is directly bonded to a nitrogen atom can be suitably used. Note that the isocyanate group-containing compound is preferably an aliphatic or alicyclic polyisocyanate. Furthermore, the isocyanate silane compound is preferably obtained by reacting the isocyanate group-containing compound and the silane coupling agent in a reaction ratio of NCO/NH=3/1 to 3/2.

The content of the isocyanate silane is preferably from 0.5 to 5.0 mass %, and more preferably from 1.0 to 2.0 mass %, in the base agent of the adhesive composition of the present technology.

Curing Agent

The curing agent of the adhesive composition of the present technology contains a compound having two or more active hydrogen groups in each molecule and at least one type of terpene compound selected from the group consisting of monoterpenes, hydrogenated monoterpenes, and modified monoterpenes formed by modifying these with hydroxy groups.

Compound Having Two or More Active Hydrogen Groups in Each Molecule

The compound having two or more active hydrogen groups in each molecule contained in the curing agent of the adhesive composition of the present technology is a component that cures the urethane prepolymer contained in the base agent described above (curing agent component in a narrow sense).

In the present technology, examples of the compound having two or more active hydrogen groups in each molecule include the same compounds as those exemplified as the active hydrogen compound used in the production of the urethane prepolymer described above. Among these, a polyol compound is preferable.

In particular, use of a polyol compound having a hydrophobic backbone, such as polybutadiene diol, as the polyol compound is preferable because superior adhesion to a resin material is achieved and especially excellent water-resistant adhesion is achieved. Furthermore, combined use with rosin diol is preferable because even better adhesion to a resin material is achieved.

When the compound having two or more active hydrogen groups in each molecule contains a polyol compound, from 80 to 100 mass % (more preferably from 90 to 100 mass %, and even more preferably 100 mass %) of the polyol compound is preferably contained in the compound having two or more active hydrogen groups in each molecule.

Terpene Compound

The terpene compound contained in the curing agent of the adhesive composition of the present technology is at least one type of terpene compound selected from the group consisting of monoterpenes, hydrogenated monoterpenes, modified monoterpenes formed by modifying the monoterpenes or the hydrogenated monoterpenes with hydroxy groups, and oligomers having from 2 to 6 repeating units derived from the monoterpenes or the modified monoterpenes.

Note that "terpene" is a series of compounds based on the isoprene rule, i.e. a generic name of compounds represented by the molecular formula: $(C_5H_8)_n$. Among these, "monoterpene" is a compound represented by the molecular formula: $(C_5H_8)_2$. Furthermore, "oligomers having from 2 to 6 repeating units derived from the monoterpenes or the modified monoterpenes" is a compound having from 2 to 6 repeating units represented by a skeleton of the monoterpene and by the molecular formula: $(C_5H_8)_2$, and may be a homopolymer (homooligomer) or may be a copolymer (cooligomer).

Among these terpene compounds, from the perspective of achieving superior initial adhesion (adherence) (hand peel test result after 60° C.×30 minutes), the terpene compound is preferably at least one type selected from the group consisting of monoterpenes, hydrogenated monoterpenes, and modified monoterpenes formed by modifying the monoterpenes or the hydrogenated monoterpenes with hydroxy groups.

Monoterpene

Examples of the monoterpene include a compound represented by Formula (1) below (α-pinene), a compound represented by Formula (2) below (β-pinene), a compound represented by Formula (3) below (limonene), myrcene, carvone, camphor, and the like. One type of these may be used alone or two or more types of these may be used in combination.

Among these, the compounds represented by Formulas (1) to (3) below are preferable.

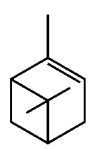

(1)

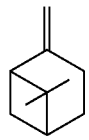

(2)

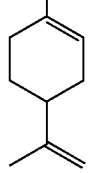

(3)

Hydrogenated Monoterpene

The hydrogenated monoterpene is a terpene compound obtained by hydrogenating the monoterpene described above.

Examples of the hydrogenated monoterpene include a compound represented by Formula (4) below (p-menthane) and the like.

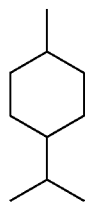

(4)

Modified Monoterpene

The modified monoterpene is a monoterpene formed by modifying the monoterpene or the hydrogenated monoterpene with a hydroxy group.

Examples of the modified monoterpene include a compound represented by Formula (5) below (α-terpineol), a compound represented by Formula (6) below (β-terpineol), a compound represented by Formula (7) below (γ-terpineol), and the like. One type of these may be used alone or two or more types of these may be used in combination.

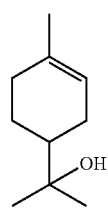

(5)

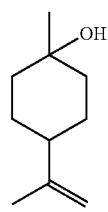

(6)

(7)

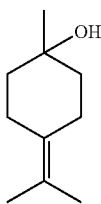

Oligomer

The oligomer is a compound having from 2 to 6 repeating units derived from the monoterpene or the modified monoterpene (but except the modified monoterpene obtained by modifying the hydrogenated monoterpene described above with a hydroxy group).

Examples of the oligomer include a compound represented by Formula (8) below (terpene resin), a compound represented by Formula (9) below (aromatic modified terpene resin), a compound represented by Formula (10) below (terpene phenol resin), and the like. One type of these may be used alone or two or more types of these may be used in combination.

(8)

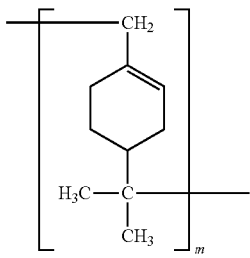

(9)

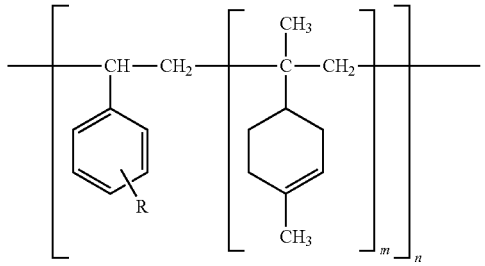

(10)

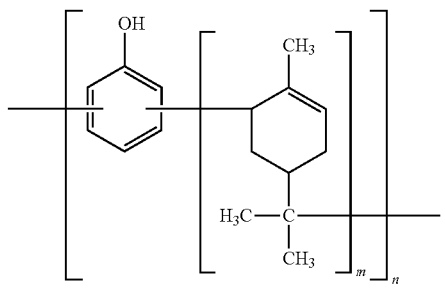

Note that, in Formulas (8) to (10) above, m represents a number from 2 to 6, n represents a number from 1 to 3, and m×n is a number from 2 to 6.

Furthermore, m and m×n are each preferably a number from 2 to 5, and more preferably a number from 2 to 3.

Meanwhile, in Formula (9) above, R represents a hydrogen atom or an alkyl group having from 1 to 12 carbons.

Furthermore, R is preferably a hydrogen atom or an alkyl group having from 1 to 4 carbons, and more preferably a hydrogen atom.

Among the terpene compounds described above, from the perspectives of generating less odor and achieving excellent workability, the oligomer is preferable, and the compounds represented by Formulas (8) to (10) above are more preferable.

The content of the terpene compound is preferably from 0.1 to 30 mass %, more preferably 0.1 mass % or greater but less than 10 mass %, and even more preferably from 2 to 6 mass %, in the curing agent of the adhesive composition of the present technology. In particular, when the content is in the range of 0.1 mass % or greater but less than 10 mass %, superior adhesion (adherence) (hand peel test after 90° C.×1 month) after heat aging is achieved.

Silane Coupling Agent

The curing agent of the adhesive composition of the present technology preferably contains a silane coupling agent from the perspective of achieving even better adhesion of the adhesive composition of the present technology.

The silane coupling agent preferably contains an active hydrogen group, and examples thereof include aminoalkoxysilanes, mercaptoalkoxysilanes, and the like.

Preferred examples of the aminoalkoxysilane include, specifically, N,N-bis[(3-trimethoxysilyl)propyl]amine, N,N-bis[(3-triethoxysilyl)propyl]amine, N,N-bis[(3-tripropoxysilyl)propyl]amine, 3-(n-butylamino)propyltrimethoxysilane, N-phenyl-γ-aminopropyltrimethoxysilane, and the like.

Preferred examples of the mercaptoalkoxysilane include, specifically, 3-mercaptopropyltrimethoxysilane and the like.

In the present technology, the compounding ratio of the base agent to the curing agent in the adhesive composition of the present technology is a ratio in which the molar ratio of the isocyanate group in the base agent to the active hydrogen group in the curing agent (NCO/OH) is preferably from 1.0 to 10.0, and more preferably from 1.5 to 2.5.

Optional Component

The adhesive composition of the present technology may contain, if necessary, various additives, in a range that does not inhibit the object of the present technology, such as fillers, curing catalysts, plasticizers, anti-aging agents, antioxidants, pigments (dyes), thixotropic agents, ultraviolet absorbers, flame retardants, surfactants (including leveling agents), dispersing agents, dehydrating agents, adhesion promoters, and antistatic agents.

The filler can be an organic or inorganic filler of any form. Specific examples thereof include fumed silica, calcined silica, precipitated silica, pulverized silica, molten silica; diatomaceous earth; iron oxide, zinc oxide, titanium oxide, barium oxide, magnesium oxide; calcium carbonate, heavy calcium carbonate, precipitated calcium carbonate (light calcium carbonate), colloidal calcium carbonate, magnesium carbonate, zinc carbonate; pyrophyllite clay, kaolin clay, calcined clay; carbon black; fatty acid-treated products, resin acid-treated products, urethane compound-treated products, and fatty acid ester-treated products thereof, and the like. One type of these may be used alone, or two or more types may be used in combination.

Although the curing catalyst is not particularly limited, specific examples thereof include carboxylic acids such as 2-ethylhexanoic acid and oleic acid; phosphoric acids such as polyphosphoric acid, ethyl acid phosphate, and butyl acid phosphate; bismuth catalysts such as bismuth octylate; tin catalysts such as dibutyltin dilaurate and dioctyltin dilaurate;

tertiary amine catalysts such as 1,4-diazabicyclo[2.2.2]octane and 2,4,6-tris(dimethylaminomethyl)phenol (e.g. DMP-30); and the like.

Specific examples of the plasticizer include diisononyl phthalate (DINP); dioctyl adipate, isodecyl succinate; diethylene glycol dibenzoate, pentaerythritol ester; butyl oleate, methyl acetyl ricinoleate; tricresyl phosphate, trioctyl phosphate; propylene glycol adipate polyester, butylene glycol adipate polyester, and the like. One type of these may be used alone or two or more types of these may be used in combination.

Specific examples of the anti-aging agent include compounds such as a hindered phenol compound.

Specific examples of the antioxidant include butylhydroxytoluene (BHT), butylhydroxyanisole (BHA), and the like.

Specific examples of the pigment include inorganic pigments such as titanium oxide, zinc oxide, ultramarine, iron red, lithopone, lead, cadmium, iron, cobalt, aluminum, hydrochloride, and sulfate; and organic pigments such as azo pigments, phthalocyanine pigments, quinacridone pigments, quinacridonequinone pigments, dioxazine pigments, anthrapyrimidine pigments, anthanthrone pigments, indanthrone pigments, flavanthrone pigments, perylene pigments, perinone pigments, diketopyrrolopyrrole pigments, quinonaphthalone pigments, anthraquinone pigments, thioindigo pigments, benzimidazolone pigments, isoindoline pigments, and carbon black; and the like.

Specific examples of the thixotropic agent include Aerosil (manufactured by Nippon Aerosil), Disparlon (manufactured by Kusumoto Chemicals, Ltd.), and the like.

Specific examples of the adhesion promoter include phenol resins, rosin resins, xylene resins, and the like.

Specific examples of the flame retardant include chloroalkyl phosphates, dimethyl-methyl phosphonates, bromine-phosphorus compounds, ammonium polyphosphates, neopentyl bromide polyethers, brominated polyethers, and the like.

Specific examples of the antistatic agent include quaternary ammonium salts; hydrophilic compounds such as polyglycols, ethylene oxide derivatives; and the like.

The method of producing the adhesive composition of the present technology is not particularly limited. For example, the adhesive composition can be prepared by a method in which a base agent containing a urethane prepolymer and a curing agent containing a compound having two or more active hydrogen groups in each molecule and a terpene compound are sufficiently mixed separately in a nitrogen gas atmosphere.

Furthermore, in the present technology, the prepared base agent can be filled and stored in a container that has been purged with a nitrogen gas or the like, and the prepared curing agent can be filled and stored in another container, and then preparation can be performed by sufficiently mixing the base agent and the curing agent at the time of use.

EXAMPLES

The present technology is described below in detail using examples. However, no such limitation to the present technology is intended.

Examples 1 to 22 and Comparative Examples 1 to 3

Each of the curing agents shown in Table 1 was obtained by mixing the components in Table 1 below according to the compositions shown in Table 1 (part by mass) using a mixer.

Thereafter, 10 g of the obtained curing agent and 100 g of the base agent (one-part urethane moisture-curable composition containing isocyanate silane, WS-252A, manufactured by the Yokohama Rubber Co., Ltd.) were mixed to obtain an adhesive composition.

Each of the obtained adhesive compositions was evaluated for adhesion by the methods described below. The results are shown in Table 1.

Adhesion (Shear Strength)

Two pieces of adherends formed by subjecting one face of a substrate (width: 25 mm, length: 120 mm, thickness: 3 mm) formed from an olefin resin to a flame treatment were prepared.

After the flame treatment, it was confirmed that the wettability on the surface of the resin was 45.0 mN/m or greater, using the Wetting Tension Test Mixture (manufactured by Wako Pure Chemical Industries, Ltd.).

The adhesive composition immediately after the preparation (mixing) was then applied to the surface of one adherend (the face on which the flame treatment was performed) so that the thickness was 3 mm. Thereafter, the coated surface was adhered to the surface of another adherend (the face on which the flame treatment was performed) and compression-bonded to produce a test sample.

After the produced test sample was left under the following condition, tensile test was performed at 23° C. in accordance with JIS K 6850:1999 to measure the shear strength (MPa). The results are shown in Table 1 below.

Condition 1: left in an oven at 60° C. for 30 minutes

Condition 2: left in an oven at 20° C. for 72 hours

Condition 3: left in an oven at 20° C. for 72 hours and then further left in an oven at 90° C. for 1 month Adhesion (Failure State)

For the test sample used for measuring the shear strength, failure state was visually observed, and the case where the cohesive failure was observed in the adhesive was evaluated as "CF", and the case where the interfacial failure was observed between the adherend and the adhesive was evaluated as "AF". The results are shown in Table 1 below.

Hand Peel Test

The test sample produced in the same condition as that for the shear strength test was left in the same conditions as those for the shear strength test (Conditions 1 to 3 described above), the adherends constituting the test sample were peeled off by hand to perform the hand peel test. At this time, the separated state of the test sample was evaluated based on the following criteria. The results are shown in Table 1.

Excellent: CF 95% or greater

Good: CF 80% or greater but less than 95%

Poor: CF less than 80%

TABLE 1

|  | Comparative Examples | | | Examples | | | |
| --- | --- | --- | --- | --- | --- | --- | --- |
| Curing agent composition | 1 | 2 | 3 | 1 | 2 | 3 | 4 |
| Polybutadiene diol | 30.0 | 30.0 | 30.0 | 30.0 | 30.0 | 30.0 | 30.0 |
| Polyether polyol | | | | | | | |
| Rosin diol | 20.0 | 20.0 | 20.0 | 20.0 | 20.0 | 20.0 | 20.0 |
| Pinene | | | | 3.0 | 30.0 | | |
| Limonene | | | | | | 15.0 | |
| Terpineol | | | | | | | 1.0 |
| P-menthane | | | | | | | |
| Terpene phenol resin | | | | | | | |
| Terpene resin | | | | | | | |
| Terpene polymer | | 3.0 | | | | | |
| Sesquiterpene | | | 3.0 | | | | |
| Calcium carbonate | 49.0 | 46.0 | 46.0 | 46.0 | 19.0 | 34.0 | 48.0 |
| Tertiary amine catalyst | 0.5 | 0.5 | 0.5 | 0.5 | 0.5 | 0.5 | 0.5 |
| Tin catalyst | 0.5 | 0.5 | 0.5 | 0.5 | 0.5 | 0.5 | 0.5 |
| Total | 100.0 | 100.0 | 100.0 | 100.0 | 100.0 | 100.0 | 100.0 |
| After 60° C. × 30 minutes | | | | | | | |
| Shearing test — Shear strength (MPa) | 0.5 | 0.7 | 0.7 | 1.3 | 1.1 | 1.2 | 1.4 |
| Shearing test — Failure state | AF | AF | AF | CF | CF | CF | CF |
| Hand peel test — Failure state | Poor | Poor | Poor | Excellent | Excellent | Excellent | Excellent |
| After 20° C. × 72 hours | | | | | | | |
| Shearing test — Shear strength (MPa) | 2.7 | 1.8 | 4.8 | 5.1 | 4.4 | 4.7 | 5.3 |
| Shearing test — Failure state | AF | AF | CF | CF | CF | CF | CF |
| Hand peel test — Failure state | Poor | Poor | Good | Excellent | Good | Excellent | Excellent |
| After 90° C. × 1 month | | | | | | | |
| Shearing test — Shear strength (MPa) | 5.1 | 4.4 | 4.1 | 5.4 | 4.6 | 5.1 | 6.0 |
| Shearing test — Failure state | CF | CF | CF | CF | CF | CF | CF |
| Hand peel test — Failure state | Good | Good | Good | Excellent | Good | Good | Excellent |

|  | Examples | | | | | |
| --- | --- | --- | --- | --- | --- | --- |
| Curing agent composition | 5 | 6 | 7 | 8 | 9 | 10 |
| Polybutadiene diol | 30.0 | 30.0 | 30.0 | 30.0 | 50.0 | |
| Polyether polyol | | | | | | 30.0 |
| Rosin diol | 20.0 | 20.0 | 20.0 | 20.0 | | 20.0 |
| Pinene | | | | | | |
| Limonene | 2.0 | | | | 15.0 | 15.0 |
| Terpineol | 1.0 | 15.0 | 30.0 | | | |
| P-menthane | | | | 15.0 | | |
| Terpene phenol resin | | | | | | |
| Terpene resin | | | | | | |
| Terpene polymer | | | | | | |
| Sesquiterpene | | | | | | |
| Calcium carbonate | 46.0 | 34.0 | 19.0 | 34.0 | 34.0 | 34.0 |
| Tertiary amine catalyst | 0.5 | 0.5 | 0.5 | 0.5 | 0.5 | 0.5 |
| Tin catalyst | 0.5 | 0.5 | 0.5 | 0.5 | 0.5 | 0.5 |
| Total | 100.0 | 100.0 | 100.0 | 100.0 | 100.0 | 100.0 |
| After 60° C. × 30 minutes | | | | | | |
| Shearing test — Shear strength (MPa) | 1.6 | 1.2 | 1.0 | 1.2 | 1.3 | 1.0 |
| Shearing test — Failure state | CF | CF | CF | CF | CF | CF |
| Hand peel test — Failure state | Excellent | Excellent | Excellent | Excellent | Excellent | Excellent |

TABLE 1-continued

| | | | | | | | |
|---|---|---|---|---|---|---|---|
| After 20° C. × 72 hours | | | | | | | |
| Shearing test | Shear strength (MPa) | 5.3 | 4.8 | 4.0 | 4.7 | 4.7 | 4.7 |
| | Failure state | CF | CF | CF | CF | CF | CF |
| Hand peel test | Failure state | Excellent | Excellent | Good | Excellent | Excellent | Excellent |
| After 90° C. × 1 month | | | | | | | |
| Shearing test | Shear strength (MPa) | 6.3 | 4.0 | 3.7 | 4.9 | 4.9 | 4.9 |
| | Failure state | CF | CF | CF | CF | CF | CF |
| Hand peel test | Failure state | Excellent | Good | Good | Good | Good | Good |

| | | Examples | | | | | |
|---|---|---|---|---|---|---|---|
| Curing agent composition | | 11 | 12 | 13 | 14 | 15 | 16 |
| Polybutadiene diol | | 10.0 | 10.0 | 10.0 | 10.0 | 10.0 | 10.0 |
| Polyether polyol | | 35.0 | 26.5 | 25.5 | 25.5 | 35.0 | 26.5 |
| Rosin diol | | | | | | | |
| Pinene | | | | | | | |
| Limonene | | | | | | | |
| Terpineol | | | | | | | |
| P-menthane | | | | | | | |
| Terpene phenol resin | | 0.5 | 9.0 | 10.0 | 20.0 | | |
| Terpene resin | | | | | | 0.5 | 9.0 |
| Terpene polymer | | | | | | | |
| Sesquiterpene | | | | | | | |
| Calcium carbonate | | 53.5 | 53.5 | 53.5 | 43.5 | 53.5 | 53.5 |
| Tertiary amine catalyst | | 0.5 | 0.5 | 0.5 | 0.5 | 0.5 | 0.5 |
| Tin catalyst | | 0.5 | 0.5 | 0.5 | 0.5 | 0.5 | 0.5 |
| Total | | 100.0 | 100.0 | 100.0 | 100.0 | 100.0 | 100.0 |
| After 60° C. × 30 minutes | | | | | | | |
| Shearing test | Shear strength (MPa) | 1.1 | 1.3 | 1.2 | 1.1 | 1.4 | 1.3 |
| | Failure state | CF | CF | CF | CF | CF | CF |
| Hand peel test | Failure state | Good | Good | Good | Good | Good | Good |
| After 20° C. × 72 hours | | | | | | | |
| Shearing test | Shear strength (MPa) | 4.6 | 4.2 | 4.0 | 3.5 | 4.2 | 4.4 |
| | Failure state | CF | CF | CF | CF | CF | CF |
| Hand peel test | Failure state | Excellent | Excellent | Excellent | Good | Excellent | Excellent |
| After 90° C. × 1 month | | | | | | | |
| Shearing test | Shear strength (MPa) | 3.8 | 3.7 | 3.5 | 3.2 | 3.9 | 3.8 |
| | Failure state | CF | CF | CF | CF | CF | CF |
| Hand peel test | Failure state | Excellent | Excellent | Good | Good | Excellent | Excellent |

| | Examples | | | | | |
|---|---|---|---|---|---|---|
| Curing agent composition | 17 | 18 | 19 | 20 | 21 | 22 |
| Polybutadiene diol | 10.0 | 10.0 | | | | |
| Polyether polyol | 25.5 | 25.5 | 62.5 | 55.4 | 55.4 | 45.4 |
| Rosin diol | | | | | | |
| Pinene | | | | | | |
| Limonene | | | | | | |
| Terpineol | | | | | | |
| P-menthane | | | | | | |

TABLE 1-continued

| | | | | | | | |
|---|---|---|---|---|---|---|---|
| Terpene phenol resin | | | | 0.7 | 4.5 | 5.0 | 10.0 |
| Terpene resin | | 10.0 | 20.0 | 0.7 | 4.5 | 5.0 | 10.0 |
| Terpene polymer | | | | | | | |
| Sesquiterpene | | | | | | | |
| Calcium carbonate | | 53.5 | 43.5 | 35.5 | 35.0 | 34.0 | 34.0 |
| Tertiary amine catalyst | | 0.5 | 0.5 | 0.4 | 0.4 | 0.4 | 0.4 |
| Tin catalyst | | 0.5 | 0.5 | 0.2 | 0.2 | 0.2 | 0.2 |
| Total | | 100.0 | 100.0 | 100.0 | 100.0 | 100.0 | 100.0 |
| After 60° C. × 30 minutes | | | | | | | |
| Shearing test | Shear strength (MPa) | 1.3 | 1.0 | 1.2 | 1.4 | 1.3 | 1.1 |
| | Failure state | CF | CF | CF | CF | CF | CF |
| Hand peel test | Failure state | Good | Good | Good | Good | Good | Good |
| After 20° C. × 72 hours | | | | | | | |
| Shearing test | Shear strength (MPa) | 4.0 | 3.8 | 4.5 | 4.0 | 3.9 | 3.7 |
| | Failure state | CF | CF | CF | CF | CF | CF |
| Hand peel test | Failure state | Excellent | Excellent | Excellent | Excellent | Excellent | Good |
| After 90° C. × 1 month | | | | | | | |
| Shearing test | Shear strength (MPa) | 3.5 | 3.3 | 4.0 | 3.6 | 3.8 | 3.2 |
| | Failure state | CF | CF | CF | CF | CF | CF |
| Hand peel test | Failure state | Good | Good | Excellent | Excellent | Good | Good |

The details of each component shown in Table 1 above are as follows.

Polybutadiene diol: R-15 HT (manufactured by Idemitsu Kosan Co., Ltd.)
Polyether polyol: EXCENOL 2020 (manufactured by Asahi Glass Co., Ltd.)
Rosin diol: D-6011 (manufactured by Arakawa Chemical Industries, Ltd.)
Pinene: α-Pinene (manufactured by Yasuhara Chemical Co., Ltd.)
Limonene: D-limonene (manufactured by Yasuhara Chemical Co., Ltd.)
Terpineol: Terpineol (manufactured by Yasuhara Chemical Co., Ltd.)
P-menthane: Para-menthane (manufactured by Yasuhara Chemical Co., Ltd.)
Terpene phenol resin: Compound represented by Formula (10) above (YS resin CP, m in the formula is 2 to 3, n in the formula is 1 to 2, manufactured by Yasuhara Chemical Co., Ltd.)
Terpene resin: Compound represented by Formula (8) above (Dimerone, m in the formula is 2 to 5, manufactured by Yasuhara Chemical Co., Ltd.)
Terpene polymer: Polymer having from 7 to 10 repeating units derived from monoterpene (PX300N, manufactured by Yasuhara Chemical Co., Ltd.)
Sesquiterpene: Terpene having two repeating units represented by the molecular formula $(C_5H_8)_2$ that was not derived from monoterpene (Longifolene, manufactured by Yasuhara Chemical Co., Ltd.)
Calcium carbonate: Super #2000 (manufactured by Maruo Calcium Co., Ltd.)
Tertiary amine catalyst: Methyl-DABCO (manufactured by Air Products and Chemicals, Inc.)
Tin catalyst: NEOSTANN U-810 (manufactured by Nitto Kasei Co., Ltd.)

From the results shown in Table 1 above, it was found that the adhesive composition prepared by blending no predetermined terpene compound exhibited poor adhesion (Comparative Example 1).

Furthermore, it was also found that the adhesive compositions prepared by blending a terpene polymer that did not correspond to the terpene compound (monoterpene) (Comparative Example 2) and by blending a trimer of terpene (Comparative Example 3) exhibited poor adhesion.

On the other hand, it was found that the adhesive compositions prepared by blending a predetermined terpene compound exhibited high shear strength and excellent adhesion to a resin material without the use of a primer (Examples 1 to 22).

In particular, when Examples 3, 6, and 8 to 10 are compared, it was found that superior adhesion was achieved in the case where the modified monoterpene (terpineol) was blended.

When Examples 1 to 22 are compared, it was found that superior initial adhesion (hand peel test: 60° C.×30 minutes) was achieved in the cases where the terpene compound other than oligomer was used (Examples 1 to 10) compared to the cases where the oligomer type terpene compound was used (Examples 11 to 22).

When Examples 11 to 22 are compared, it was found that superior adhesion after aging test (hand peel test: 90° C.×1 month) was achieved in the cases where the content of the terpene compound was less than 10 mass % (Examples 11, 12, 15, 16, 19, and 20) compared to the cases where the content of the terpene compound was 10 mass % or greater (Examples 13, 14, 17, 18, 21, and 22).

The invention claimed is:

1. A two-part curable urethane adhesive composition comprising:
   a base agent containing a urethane prepolymer, and a curing agent containing a compound having two or more active hydrogen groups in each molecule;
   the curing agent containing at least one type of terpene compound selected from the group consisting of monoterpenes, hydrogenated monoterpenes, modified monoterpenes formed by modifying the monoterpenes or the hydrogenated monoterpenes with hydroxy groups, and oligomers having from 2 to 6 repeating units derived from the monoterpenes or the modified monoterpenes.

2. The two-part curable urethane adhesive composition according to claim 1, wherein
   the monoterpene is a compound represented by Formula (1), a compound represented by Formula (2), or a compound represented by Formula (3);
   the hydrogenated monoterpene is a compound represented by Formula (4);
   the modified monoterpene is a compound represented by Formula (5), a compound represented by Formula (6), or a compound represented by Formula (7); and
   the oligomer is a compound represented by Formula (8), a compound represented by Formula (9), or a compound represented by Formula (10):

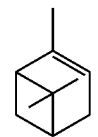 (1)

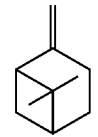 (2)

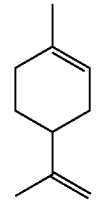 (3)

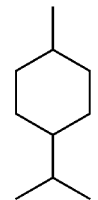 (4)

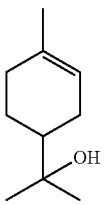 (5)

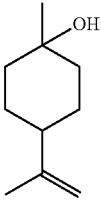 (6)

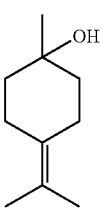 (7)

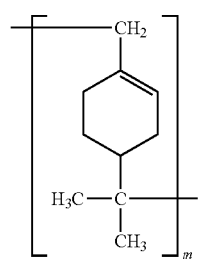 (8)

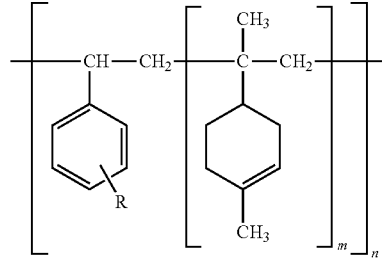 (9)

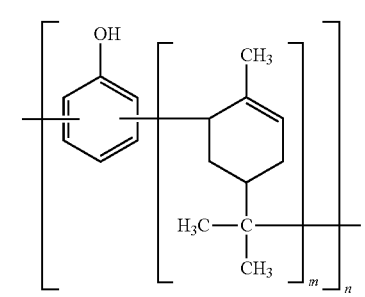 (10)

where, in Formulas (8) to (10), m represents a number from 2 to 6, n represents a number from 1 to 3, and m×n is a number from 2 to 6; and in Formula (9), R represents a hydrogen atom or an alkyl group having from 1 to 12 carbons.

3. The two-part curable urethane adhesive composition according to claim 1, wherein a content of the terpene compound is from 1 to 30 mass % relative to the total mass of the curing agent.

4. The two-part curable urethane adhesive composition according to claim 1, wherein the curing agent contains a polybutadiene diol as the compound having two or more active hydrogen groups in each molecule.

5. The two-part curable urethane adhesive composition according to claim 1, wherein the curing agent contains a rosin diol as the compound having two or more active hydrogen groups in each molecule.

6. The two-part curable urethane adhesive composition according to claim 1, wherein the base agent further contains an isocyanate silane compound.

7. The two-part curable urethane adhesive composition according to claim 1, wherein the curing agent contains a polyol compound as the compound having two or more active hydrogen groups in each molecule; and
the two-part curable urethane adhesive composition is used for adhesion to a resin material using no primer.

8. The two-part curable urethane adhesive composition according to claim 1, wherein the terpene compound is at least one type selected from the group consisting of monoterpenes, hydrogenated monoterpenes, and modified monoterpenes formed by modifying the monoterpenes or the hydrogenated monoterpenes with hydroxy groups.

9. The two-part curable urethane adhesive composition according to claim 2, wherein a content of the terpene compound is from 1 to 30 mass % relative to the total mass of the curing agent.

10. The two-part curable urethane adhesive composition according to claim 2, wherein the curing agent contains a polybutadiene diol as the compound having two or more active hydrogen groups in each molecule.

11. The two-part curable urethane adhesive composition according to claim 3, wherein the curing agent contains a polybutadiene diol as the compound having two or more active hydrogen groups in each molecule.

12. The two-part curable urethane adhesive composition according to claim 9, wherein the curing agent contains a polybutadiene diol as the compound having two or more active hydrogen groups in each molecule.

13. The two-part curable urethane adhesive composition according to claim 2, wherein the curing agent contains a rosin diol as the compound having two or more active hydrogen groups in each molecule.

14. The two-part curable urethane adhesive composition according to claim 3, wherein the curing agent contains a rosin diol as the compound having two or more active hydrogen groups in each molecule.

15. The two-part curable urethane adhesive composition according to claim 4, wherein the curing agent contains a rosin diol as the compound having two or more active hydrogen groups in each molecule.

16. The two-part curable urethane adhesive composition according to claim 9, wherein the curing agent contains a rosin diol as the compound having two or more active hydrogen groups in each molecule.

17. The two-part curable urethane adhesive composition according to claim 10, wherein the curing agent contains a rosin diol as the compound having two or more active hydrogen groups in each molecule.

18. The two-part curable urethane adhesive composition according to claim 11, wherein the curing agent contains a rosin diol as the compound having two or more active hydrogen groups in each molecule.

19. The two-part curable urethane adhesive composition according to claim 12, wherein the curing agent contains a rosin diol as the compound having two or more active hydrogen groups in each molecule.

20. The two-part curable urethane adhesive composition according to claim 2, wherein the base agent further contains an isocyanate silane compound.

\* \* \* \* \*